United States Patent
Tombült-Meyer et al.

(10) Patent No.: US 7,527,823 B2
(45) Date of Patent: May 5, 2009

(54) METHOD AND APPARATUS FOR CREATING A PULSED STREAM OF PARTICLES

(75) Inventors: Thomas Tombült-Meyer, Nettersheim (DE); Frank Hubert Frings, Mechernich (DE); Markus Borbach, Frankfurt (DE); Miguel Brandt Sanz, Wachtberg (DE); Mattias Schmidt, Idstein (DE); Peter Dziezok, Hochheim (DE); Claus-Peter Stoelzel, Bad Soden (DE); John Peter Lankhof, Bad Homburg (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/493,313

(22) Filed: Jul. 26, 2006

(65) Prior Publication Data

US 2006/0264134 A1 Nov. 23, 2006

Related U.S. Application Data

(62) Division of application No. 10/423,425, filed on Apr. 25, 2003, now abandoned.

(30) Foreign Application Priority Data

May 28, 2002 (EP) .................................. 02011785

(51) Int. Cl.
*B05D 1/12* (2006.01)
(52) U.S. Cl. ...................................... 427/197; 427/201
(58) Field of Classification Search ........................ None
See application file for complete search history.

(56) References Cited

U.S. PATENT DOCUMENTS

| | | | |
|---|---|---|---|
| 3,974,411 A | 8/1976 | Faulkner et al. | |
| 4,393,892 A | 7/1983 | Di Rosa | |
| 4,543,274 A | 9/1985 | Mulder | |
| 4,600,603 A | 7/1986 | Mulder | |
| 4,685,915 A | 8/1987 | Hasse et al. | |
| 4,770,344 A | 9/1988 | Kaiser | |
| 4,800,102 A * | 1/1989 | Takada | 427/197 |
| 4,927,346 A | 5/1990 | Kaiser et al. | |
| 5,017,324 A | 5/1991 | Kaiser et al. | |
| 5,028,224 A | 7/1991 | Pieper et al. | |
| 5,037,247 A | 8/1991 | Kaiser et al. | |
| 5,156,902 A | 10/1992 | Pieper et al. | |
| 5,213,817 A | 5/1993 | Pelley | |
| 5,248,524 A * | 9/1993 | Soderlund | 427/200 |
| 5,429,788 A | 7/1995 | Ribble et al. | |
| 5,567,472 A * | 10/1996 | Siegfried et al. | 427/180 |
| 6,026,957 A | 2/2000 | Bauer et al. | |
| 6,033,199 A * | 3/2000 | Vonderhaar et al. | 425/81.1 |
| 6,334,858 B1 | 1/2002 | Ronnberg et al. | |
| 6,444,090 B1 | 9/2002 | Wolf et al. | |

FOREIGN PATENT DOCUMENTS

WO WO92/19198 11/1992

* cited by examiner

*Primary Examiner*—Frederick J Parker
(74) *Attorney, Agent, or Firm*—Charles R. Ware; Eric T. Addington

(57) ABSTRACT

A method of producing an absorbent article, including: metering particles at a predetermined flow rate to form a metered particle stream; carrying the metered particle stream in a carrier flow to form a carried particle stream; pulsing the carried particle stream to form a pulsed particle stream; and transferring a pulse from the pulsed particle stream onto a forming surface of the absorbent article.

8 Claims, 5 Drawing Sheets

METHOD AND APPARATUS FOR CREATING A PULSED STREAM OF PARTICLES

CROSS-REFERENCE TO RELATED APPLICATIONS

This application is a divisional of prior U.S. application Ser. No. 10/423,425, filed Apr. 25, 2003, now abandoned. This application incorporates U.S. application Ser. No. 10/423,425 by reference.

FIELD OF THE INVENTION

The present invention provides a method and an apparatus for forming a pulsed stream of a particulate material, allowing high pulsing frequencies, and being particularly suitable for the production of disposable absorbent articles, such as baby diapers and the like.

The invention is further directed to a kit or pack of individual absorbent articles which can be produced using the method and the apparatus.

BACKGROUND

Creating constantly and quickly repeating pulses of particulate material suspended in a carrier means such as air has been a long lasting desire for many applications, in particular for pulses which are well controlled with regard to their shape, to their frequency, and to the amount of material transferred during these pulses. A particularly useful application is during the manufacture of disposable absorbent articles, such as baby diapers, adult incontinence or feminine hygiene pads, and the like, where the manufacturing aims at high production speed and low variability.

In U.S. Pat. No. 4,800,102 (Takada), an apparatus and method for spraying or scattering solid particulate powders onto a substrate is described. The powder is scattered onto a rotatable disc member, which has at least one opening through which a portion of the powder can pass through to reach an underlying substrate, while the non-passing powder is recycled to the powder feeder. Another masking process is described in PCT publication WO-A-92/19198 (Perneborn). Thereby, a device for depositing particles on a moving web of material has an apertured belt which moves over a material web and has a particle dispenser to dispense particles in a uniform pattern in the shape of the apertures of the belt. The particles not dispensed through the apertures are recycled back to the particle feeder.

Both of these systems use the gravity for accelerating the powder particles, and are limited in pulse frequency and hence overall production speed. Further, as part of the powder delivered to the device is recycled, there is only limited control of the amount of powder disposed on the substrate, and hence in the produced article.

U.S. Pat. No. 5,213,817 (Pelley) describes a powder spray ejector oscillating over a flow separator, which separates a portion of the powder being deposited on a web, and the other portion being recycled.

Other approaches use pulsing of an air stream to create a pulsed particle stream, such as described in U.S. Pat. No. 4,927,346 (Kaiser), U.S. Pat. No. 6,033,199 (Vonderhaar). In U.S. Pat. No. 5,028,224 (Pieper) an apparatus and process for providing a pulsed particle stream is described, wherein a continuous gas entrained stream of particles is centrifugally diverted into an accumulation region, from where it is selectively discharged, such as by the use of a pulsed air stream.

U.S. Pat. No. 4,543,274 (Mulder) discloses a powder spray gun wherein high velocity air is said to impact powder entrained air contained in the bore of the gun. U.S. Pat. No. 4,600,603 (Mulder) discloses a powder spray gun apparatus wherein an inverted flow amplifier is located adjacent to the inlet of the gun to enhance blending of powder within the gun. From the inverted flow amplifier, the blended powder is supplied to a downstream air flow amplifier which is operable to impact air entrained powder with a high velocity stream of compressed air. A powder control system controls powder supply from powder supply pumps to the spray gun. The powder pumps are said to be conventional venturi powder pumps.

U.S. Pat. No. 4,770,344 (Kaiser) discloses a powder spraying system including a volumetric or gravimetric material feeding device for metering a quantity of powder into a manifold, and air flow amplifiers connected to passageways formed in the manifold. Kaiser '344 teaches that a problem associated with venturi powder pumps is the difficulty in obtaining a consistently accurate feed rate of powder material, especially when a spray gun is operated intermittently. U.S. Pat. No. 4,927,346 and U.S. Pat. No. 5,017,324 (Kaiser) disclose additional embodiments for depositing particulate material into a pad with a spray gun, including an embodiment having an inverted flow amplifier and an embodiment having a rotating screw for providing a metered quantity of absorbent particles. U.S. Pat. No. 5,037,247 (Kaiser) discloses a powder pumping apparatus having a venturi passageway and an air ejector including a valve mechanism. Kaiser '247 teaches that it is desirable to include a valve in the air ejector to eliminate the "dead zone" in the air supply tube extending between the valve and the inlet to the pump body, and thereby eliminate the powder pulse "tailing effect" experienced in other powder pump designs. However, such an arrangement has the disadvantage of a requiring a valve assembly adjacent to or within the ejector, which may not be practical or even possible in every installation due to space or geometry constraints. These approaches have in common, that they primarily create a pulsed gas/air stream, which accelerates the particles to create a pulsed particle stream. However, such air pulses are difficult to control in stable manner, in particular for higher pulse frequencies and higher particle flow rates.

Henceforth, the present invention aims at overcoming limitations of the known systems, in particular with regard to pulse frequency so as to allow for higher production speeds, as well as with regard to higher throughput on a per pad basis, so as to satisfy the requirements of modern absorbent article design.

As a further objective the invention provides a kit or pack of individual absorbent articles in a cost effective manner.

SUMMARY

The present invention is a method of creating a pulsed stream of particles in a carrier means, which includes the steps of suspending a first metered stream of particles in a carrier means, guiding this first stream to a pulsing means, accumulating a portion of these particles in a pulsing chamber of the pulsing means, which further includes a separator means, and emptying the particles out of the pulsing means by a suction means, whereby the accumulation is performed by interrupting the stream of particles as flowing from an inlet of the pulsing means to an outlet of the pulsing means by the separator means for not less than 95%, preferably not less than 90%, more preferably not less than 75% and even more preferably not less than 50% of said time of a pulse.

Preferably, the separator means rotates in the pulsing means. It is also preferred, that the suction means is an venturi-type ejector, or a ring-jet-type coaxial ejector, preferably positioned in proximity to the outlet of the pulsing means, and that the suction means is positioned in proximity to the outlet of the pulsing means. The present invention is particularly suitable for creating pulses at a frequency of at least 10 Hz preferably more than 15 Hz, even more preferably more than 20 Hz.

In a further aspect, the present invention is an apparatus for pulsing a metered stream of particular material in a carrier means comprising, a metering means, a pulsing means having an inlet, an outlet, a pulsing chamber located there between and comprising a separator means, and a suction means arranged in proximity of the outlet. The separator means is arranged to interrupt said flow of particles between the inlet and the outlet for not less than 95%, preferably not less than 90%, more preferably not less than 75% and even more preferably not less than 50% of said time of a pulse. The separator means may be designed to not interrupt the flow of the carrier means, which preferably is a gas, such as air.

It is also preferred, that the suction means is an venturi-type ejector, or a ring-jet-type coaxial ejector, preferably positioned in proximity to the outlet of said pulsing means, and that the suction means is positioned in proximity to the outlet of said pulsing means.

In a further aspect the invention relates to a kit or pack of individual absorbent articles, the absorbent articles being produced by a method of low standard deviation manufacturing, the kit or pack of absorbent articles comprising at least 10 individual absorbent articles which have been produced consecutively by the method of low standard deviation manufacturing, the absorbent articles each comprising a topsheet and a backsheet and an absorbent core encased between the topsheet and the backsheet, the absorbent core comprising a first material providing for a first absorbent capacity and a second absorbent material providing for a second absorbent capacity, the absorbent core having a longitudinal direction, the absorbent core comprising a front half and a rear half, the halves having equal length as measured in the longitudinal direction, the front half of the absorbent core comprising more than 60% of the second absorbent capacity, the second absorbent material comprised by the absorbent material of each of the absorbent articles having a total weight, the kit or pack of absorbent articles having a average total weight taken as the average of the total weights of the particulate absorbent material of individual articles, the kit or pack of absorbent articles having a standard deviation of total weight calculated based on the deviation of the total weight of the particulate absorbent material of individual articles from the average total weight, wherein the standard deviation of total weight is less than 8%.

DETAILED DESCRIPTION OF THE INVENTION

Within the context of the present description, the term "pulse" is used to describe the time dependency of a particle flow in a certain, repeating pattern. This pattern can be described via the local flow of material per time interval (in units of g/sec) and a repeating frequency defining a time interval for the pulse.

Figure 1A:
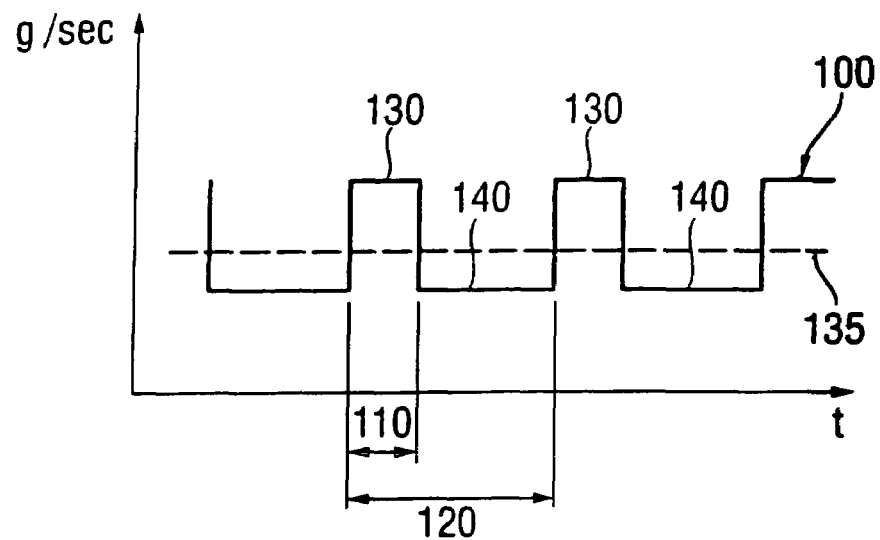
FIGS. 1A, B, C, and D show schematically diagrams of pulse patterns.

Thus, in FIG. 1A, a typical pulse pattern 100 is depicted, showing an example for a repeating particle flow pulse. The pulse has a pulse duration 110, a pulse repeating time period 120 (defining a pulse frequency), and a peak pulse flow rate 130. If there is no particle flow between two pulses, the minimum pulse flow rate 140 is equal to zero. The particle flow can be further described by the average flow rate 135. The particle flow can also be expressed by the particle density, defined by the volumetric flow of particles divided by volumetric flow of air.

Figure 1B:
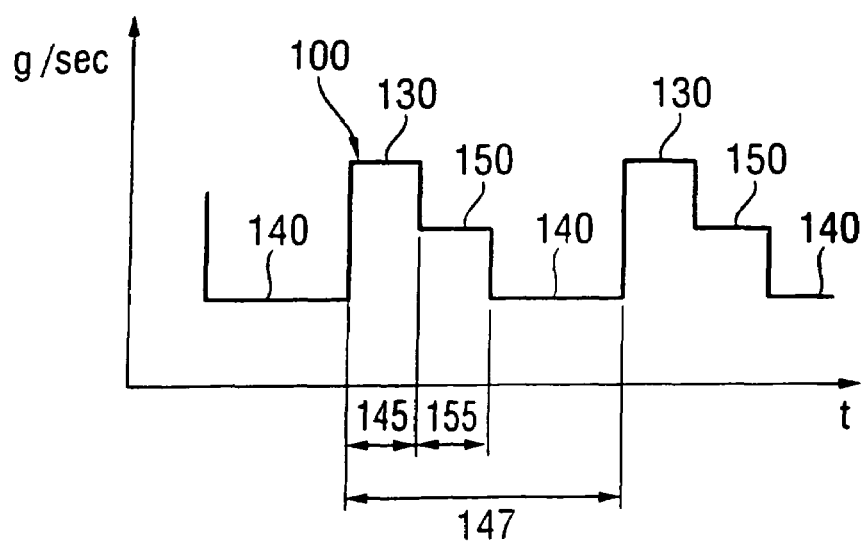
Figure 1C:
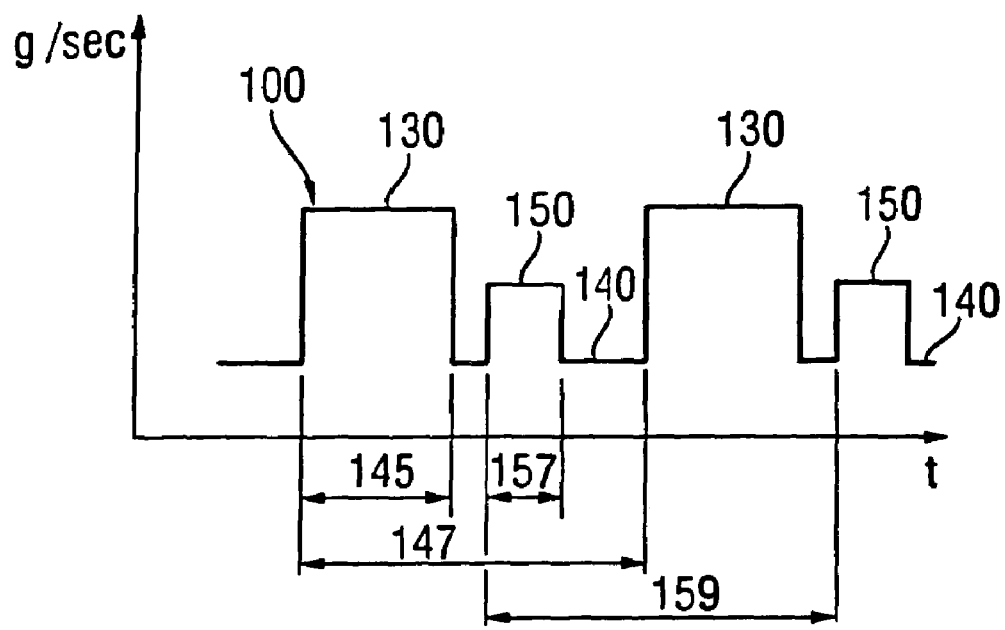

In particular cases, the pulse can have two (or even more) plateaus with a second plateau flow rate 150 for a second plateau duration time 155 (see FIG. 1B), which even further may be interrupted (see FIG. 1C), whereby a first pulse duration and frequency (145, 147) and a second pulse duration and frequency (157, 159) can be distinguished.

Figure 1D:
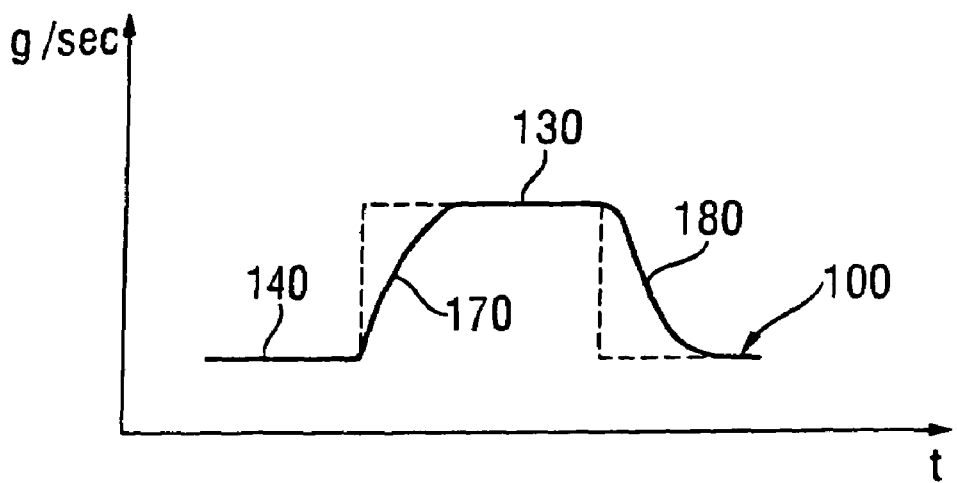

The shown rectangular "pulse shape" is certainly often desired, but generally the shape will differ to a certain extent, and in the extreme, a can be formed by gradually increasing and decreasing flanks 170, 180 (see FIG. 1D).

Within the context of the present description, the term "flow path" is used to describe the path of a moving object, such as a particle. A flow path between two locations (such as cross-sectional areas 210 and 220 of a tube 200 as shown in the schematic cross-sectional view in FIG. 2) is called uninterrupted, or continuous, if a particle can move from such a location 210 (inlet) to another location 220 (outlet) without encountering a physical barrier, as indicated by the continuous arrows 240. It is called interrupted, if a particle is hindered by physical barrier, such as schematically and exemplarily indicated by a rotary valve element 230. For this instance, there will be separated flow paths on both sides of the barrier, as indicated by the flow path arrows 245 and 247 respectively. While, of course, also movements of fluids like gases can be described flow paths (and also both continuous as well as interrupted ones), the term "particle" is used herein to describe discrete solid particles, for example in the context of disposable absorbent articles it can be absorbent particles, or superabsorbent particles, which are essentially dry particles having a particle size which can range from several microns to several millimetres. Such particles can be suspended in a "carrier", such as a gas such as air.

DESCRIPTION OF THE FEATURES OF THE PROCESS AND APPARATUS

The present invention is not limited to a particular application, and flow rates, pulse frequencies can be varied in a broad range without departing from the essence of the present invention. However, the following explanations will refer in certain aspects to specific examples, which will be—without limiting the present invention to this field—the manufacture of disposable absorbent articles, such as baby diapers and the like.

Particle Flow Metering

Metering devices to provide well defined particle mass flow rates, in particular constant predetermined flow rates, are well known in the art. Such a metering apparatus can include a hopper with, for example a screw feeder and a scale or "loss-in-weight control". A suitable metering apparatus particularly suitable in the manufacture of absorbent articles is an Acrison Volumetric Feeder, Model No. 405-105X-F, available from Acrison, Inc. of Moonachie, N.J. Such a metering apparatus can be operated to provide a mass flow rate of up to about 1500 kg/hr or more, preferably between 30 kg/hr and 1200 kg/hr.

The particle metering apparatus can be connected for further conducting the metered particle stream to a connecting means. A typical example for such a connecting means is a tube having an inner diameter of about 2.5 cm (about 1 inch). Preferably, the connector means does not have sharp edges or bends, as this might influence the stability of the particle stream.

If the metering apparatus and the pulsing means are appropriately arranged with regard to their relative positioning, there is no need for a carrier means to carry the particle from the metering apparatus to the pulsing means, but gravity would suffice to let the particles fall from the first to the second. However, often it can be advantageous to have some carrier flow, such as air flow. If an additional carrier stream is used, this is preferably done at moderate carrier speed, and in a preferred embodiment as described hereinafter, carrier velocities of between 1 and 20 m/sec have been found to be suitable. This carrier stream is further preferably steady to maintain a constant particle stream. In case of carrier flow fluctuations, these are preferably in phase with the pulsing frequency so as maintain stable conditions. For the described exemplary application in the manufacture of absorbent articles, such a carrier flow can be created by having an opening to the ambient in the connecting means, positioned close to the metering apparatus. Suction as applied on the other side of the pulsing means (and discussed hereinafter) can suffice to provide stable particle flow conditions.

An important element of the present invention is the pulsing means, arranged (in following the flow path direction of particles) after the connection means, and operated so as to create the pulsed particle flow.

The pulsing means is designed to allow interrupting the particle flow in a repeating manner, whereby the particles are accumulated during this interruption period and released thereafter. The pulsing means comprises an inlet, through which the particles can enter the pulsing means, an outlet, through which the particles can exit the pulsing means, a pulsing chamber positioned between the inlet and the outlet providing sufficient space to allow accumulation of at least some of the particles, and a separator means, positioned in this pulsing chamber.

While it may interrupt the carrier flow for a part of a cycle time, there has to be a certain time, during which the carrier flow path and a particle flow path are connected from the inlet of the pulsing means to the outlet of the pulsing means. Without wishing to be bound by the explanation, it is believed, that this period is important to stabilize the flow properties of the carrier.

A pulsing means suitable for applications such as in the production of absorbent articles can be designed to pulse a stream of absorbent particles, with typical sizes in the range of several micron to few millimetres, and with particle flow rates in the range of 1500 kg/hr or more. For such an application, pulse frequencies can range from about 3 to about 35 Hz or even more.

A suitable pulsing means in the context of the present invention impacts on the particles directly in a valve-type function. This is to be seen in contrast to other approaches, wherein a pulse of a carrier means, such as a pulsed air stream, impacts on the particles. The valve type-operation can be realized by various designs, such as oscillating slide valves, iris-type valves, diaphragm-type valves, rotating, apertured disks similar to the design as described in U.S. Pat. No. 4,800,102 (Takada).

A further exemplary and preferred pulsing means builds on the principles of a rotary valve, as is well known in the art as a closure element, such as for a storage container for particulate material. Therein, however, they are designed to hermetically separate the storage container from the subsequent system, such as a pneumatic transport system, without providing a certain period of the cycle time with a continuous particle flow path—see as one of various exemplary disclosures U.S. Pat. No. 3,974,411 (Miller). Alternatively, rotary valves are known to provide for an "open-close" functionality (i.e. no accumulation functionality as in the present case), such as described in U.S. Pat. No. 4,393,892 (Di Rosa).

One particular benefit of such rotary designs is the avoidance of oscillatory movements, which, in particular for higher frequencies, would create either undesirably heavy (and hence difficult to accelerate) elements, or designs with a non-satisfactory reliability. In contrast to these, a rotary design can keep the separator means operating at a constant speed, thus allowing a much more stable operation even for high pulse frequencies.

Figure 3A:
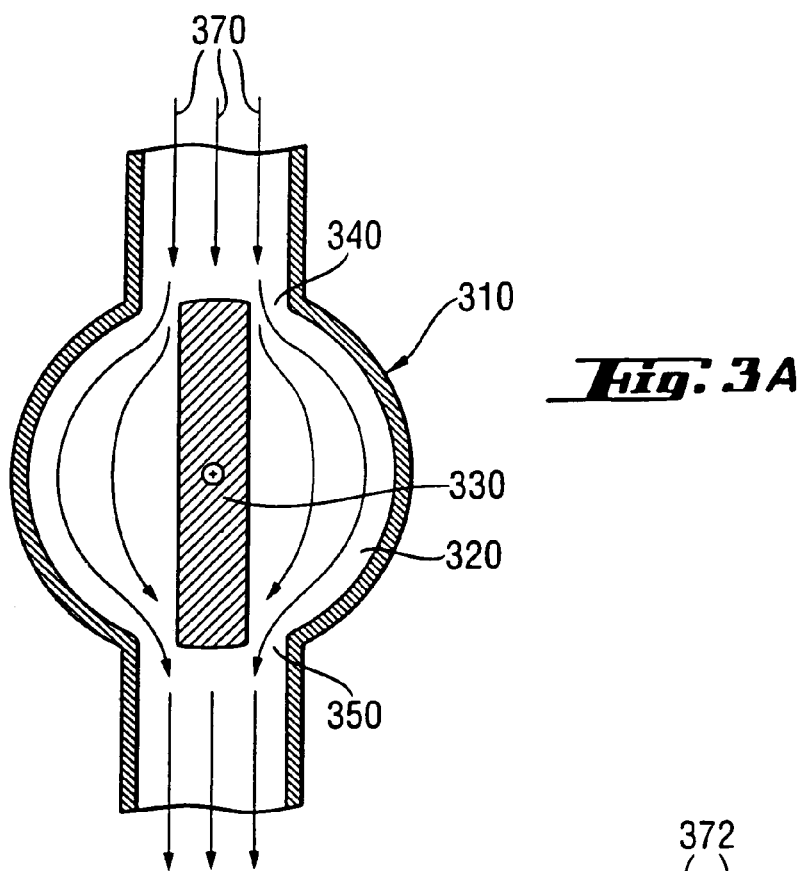
FIGS. 3A and 3B show schematic presentations of an exemplary pulsing means according to the invention.
Figure 3B:
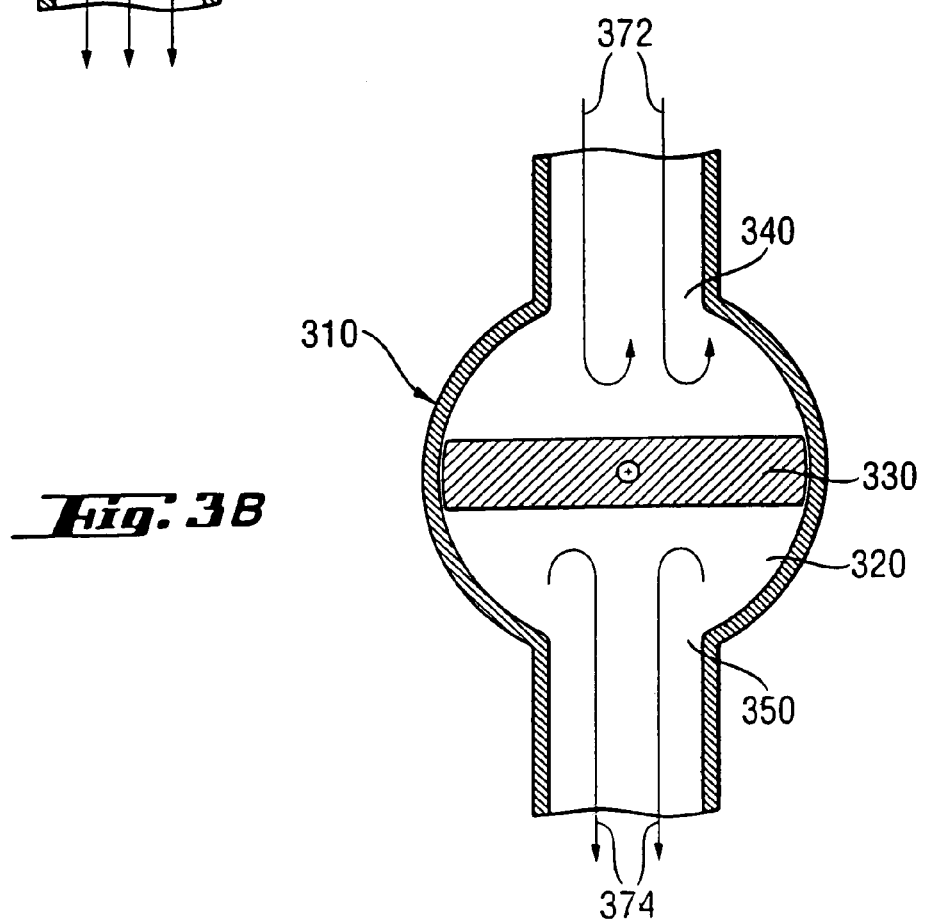

As depicted in a schematic, cross-sectional view—see FIG. 3A—such a preferred rotary pulsing means 310 can comprise a rotating separator means 330, rotatably mounted in a pulsing chamber 320, having a cylindrical shape with a diameter and a height, of the pulsing means 310. Further indicated is a particle flow path 370, freely connecting the inlet 340 and the outlet 350, without being obstructed by a separator means 330. FIG. 3B schematically shows the same equipment (with equal numerals indicating same elements), now at a different rotational position of the separator means 330, such that there is no free particle path connection between the inlet 340 and the outlet 350, but there is a filling flow path 372 disconnected from the emptying flow path 374.

When, during the operation, the separator means 330, as it rotates at a predetermined frequency, it takes the position of interrupting the particle flow path, the particles, arriving at the inlet 340 at an essentially constant stream will accumulate in that part of the pulsing chamber 320, which is connected to the inlet 340. During this time, essentially no particles will exit the pulsing means through the outlet 350. During the period where the separator means 330 is in a position so as to not interrupt the particle flow path, the chamber will essentially be emptied, and some particles may penetrate through the complete chamber, depending on the relative speed of the particles compared to the rotational speed. If these speeds are appropriately chosen, the rotation of the separator means can impact on the accumulated particles and accelerate these out of the chamber.

For the exemplary application in the production process of manufacturing disposable absorbent articles, the diameter of the pulsing chamber can suitably be in the range of 50 to 500 mm, with a diameter of 120 mm working well. The thickness dimension (i.e. along an axis perpendicular to the plane of FIG. 3) can suitably be in the range of about 10 to about 100 mm, with a thickness of 50 mm found to be working well.

For a symmetrically shaped separator means 330 as indicated in FIG. 3, one 360° rotation of the separator means will result in creating two pulses, i.e. the pulse frequency is twice the rotational frequency.

Figure 4A:
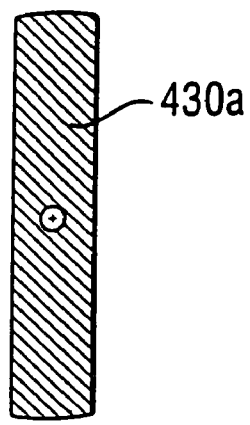
FIGS. 4A through 4C show exemplary embodiments for separator means useful in such a pulsing means.
Figure 4B:
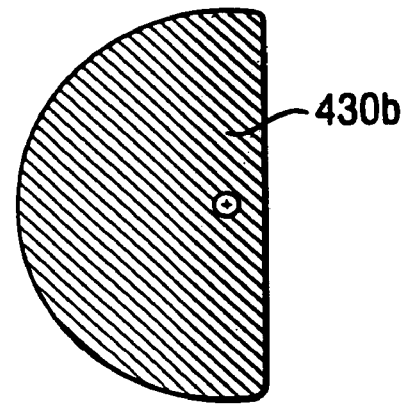
Figure 4C:
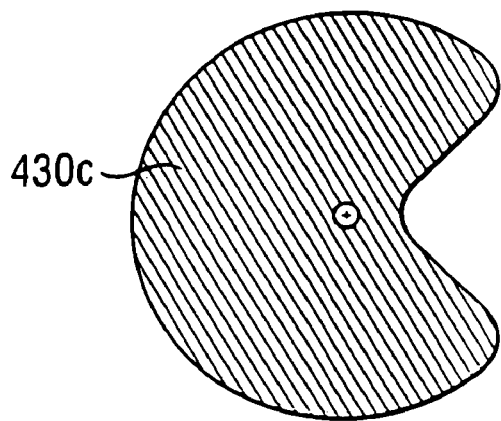

The separator means 330 can be an essentially rectangular bar with its ends being rounded to fit smoothly into the cylindrical separator chamber without undue friction or gapping. The separator means can also have different shapes, provided it enables the separation function by smoothly fitting to the walls of the separator chamber. For example, it can have essentially oval cross-section, or ellipsoidal shape, or others as indicated in FIG. 4 A to C (see separator means 430a-430c). The shape of the separator means can be used to design the shape of the resulting pulses, in particular to create stepped pulses, or two subsequent pulses with differing pulse form. An asymmetric design of the separator means results in two pulses per one 360° rotation of the separator means, each with a different pulse shape. FIG. 4B shows an essentially semi-circular cross-section. Such a design would provide one accumulation phase for one rotation of the separator means.

Figure 2A:
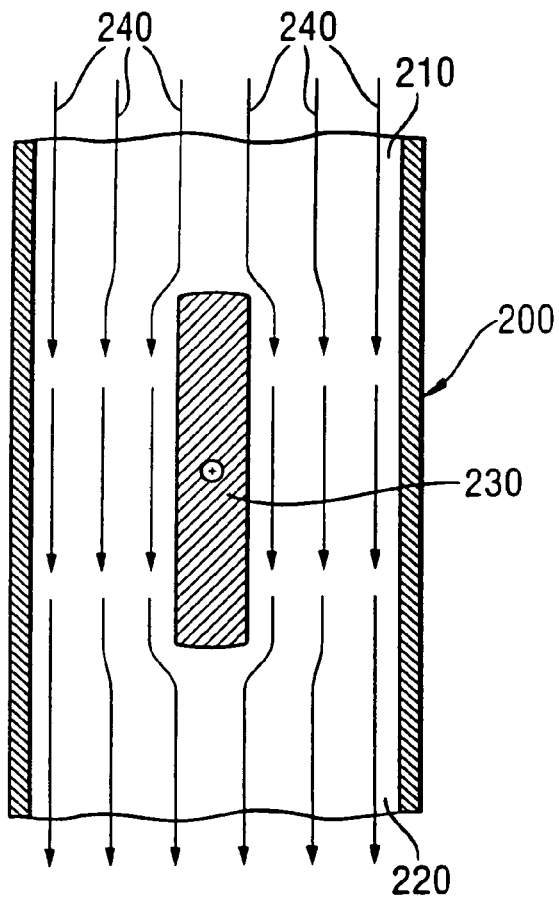
FIGS. 2A and 2B show schematic presentation of an uninterrupted, continuous particle flow path (FIG. 2A), and an interrupted flow path (FIG. 2B).
Figure 2B:
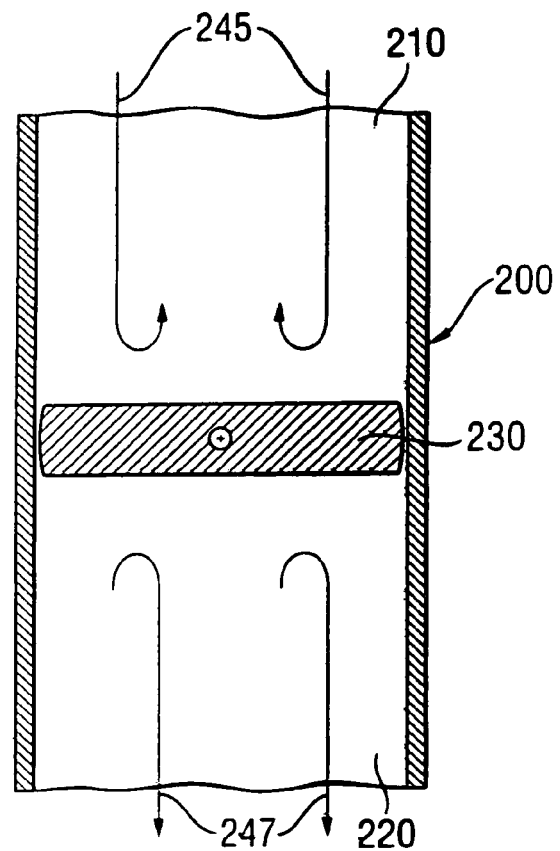

While in FIGS. 2 and 3 the inlet and the outlet have been shown in a particular relative positioning (in a 180° degree arrangement), this does not need to be the case. It will be clear to a skilled person that the relative positioning of inlet and outlet to each other will impact on the pulse shape in cooperation with the shape of the separator means. Thus, for many applications, the 180° design will be most suitable, but this does not need to be always the most preferred execution. Also, for the inlet and the outlet duct there does not need to be a radial arrangement of the connector means (as shown in FIGS. 2 and 3), but more tangential or even curved tangential designs can be preferred. It has been found that more tangential outlet could deliver a significantly higher throughput of particles compared to a perpendicular outlet. Similarly, the size of the inlet and outlet openings can be equal, such that the projected area ratio of the two is about one. A skilled person will readily find out the balance of simplicity of design, match with other fittings of the apparatus, and, of course, the desire for maintaining the pulse shape adequately.

In order to transfer the particles from the pulsing chamber to the further steps of the process, suction is applied to empty the pulsing chamber effectively. In the exemplary process of manufacturing absorbent articles, the forming of such articles often comprises the step of laying down absorbent materials—such as the particles undergoing the pulsing step—on a forming means, such as a permeable carrier, by applying vacuum on the side facing away from the feeding and pulsing means. Then, this vacuum can suffice to create suction for emptying the separator chamber, and an opening positioned close to the outlet of the pulsing chamber can provide sufficient carrier flow.

Under certain conditions it will be desired to not only empty the pulsing chamber quickly, but also to accelerate the particles to a relatively higher speed. Such instances can be for example the mixing of these particles with other matter, such as fibres, like cellulose fibres, staple synthetic fibres meltblown fibres or the like, in the case when forming absorbent articles. Such acceleration should preferably not distort the pulse shape as created by the pulsing means. Then, a particular suction means can be positioned between the pulsing chamber and the forming means.

It is important, that the suction means does not distort the shape of the pulse too much, such as for example a rotary ventilator would do. It has been found suitable to use an additional stream of carrier, such as gas or air, so as to accelerate the carrier stream and thereby also the particle pulse stream. A venturi type ejector has been found suitable if used to provide moderate suction and hence acceleration. For higher suction and acceleration, such venturi type ejectors tend to provide a non-uniform flow pattern across the cross-section, generally in the shape a pronounced parabolic profile. However, in order to maintain the shape of the pulse, a more rectangular, or "plug flow" profile is preferred.

A suitable element to provide such flow characteristics has been found in a coaxial eductor. Two design principles have been found to be particularly suitable each for certain circumstances:

a) A ring jet ejector, which use is based on the well known Coanda effect, has been found to be working extremely well especially for lower particle density streams (i.e. lower average particle flow rates) which need to get accelerated to very high speeds. This is due to the fact that Coanda effect based ejector designs deliver the highest suction air volume stream at least for carrier-only systems. Coanda flow tends to stall if the particle density is too high.

The design of these ejectors even more preferably has a fixed gap design. Such ejectors can be produced by EXAIR (Cincinnati, Ohio, USA) under the designation Air Amplifier 6032, or Krahnen (Cologne, Germany) under the designation RJ25. It has further been found, that such ejectors can provide velocities of the carrier of up to of 80 m/sec or even more with a much more levelled velocity profile.

b) A coaxial ejector designed to use the Venturi effect has been found to be less critical to higher particle densities (volumetric flow of particles divided by volumetric flow of air). Such ejectors still deliver plug flow type of speed profiles, which preserve the pulse, as delivered from the separator mean. Such ejectors can be produced by EXAIR (Cincinnati, Ohio, USA) Line Vac 6063. These devices may need modification to increase suction air by increasing the motive air, such as by increasing the number of air throughput holes.

A particular benefit of such an arrangement is, in addition to providing a sharply defined pulse, an even profile throughout this pulse. In particular, it allows avoiding of a bias in the profile, such as a particle distribution to the left or right side of a system.

In order to allow a more effective emptying of the pulsing chamber, the suction means is preferably positioned in the proximity of the outlet of the chamber, more preferable immediately adjacent thereto. To change the profile this may be changed according to the application need i.e., if the slope of the density change should be less steep a longer distance would be appropriate.

Once the pulsed particle stream has been created, and optionally accelerated, the transfer to the downstream process steps can be done in any conventional manner as well know to the skilled person, and as described in the above referenced documents. As indicated in the above, such process steps can include mixing of the pulsed particle stream with other materials, such as in the exemplary application of forming absorbent articles with fibres, which can be a continuous stream, or discontinuous. The pulsed stream can also be laid down on a forming means, such as a screen or web permeable to the carrier but not to the particles. Preferably, the distance to the subsequent process steps is not too long so as to allow maintaining the pulse shape.

Preferred Products and Kits or Packs of Products

Preferably the method of creating a pulsed stream of particles is used for the production of absorbent articles, such as baby diapers, training pants, adult diapers or incontinence products, sanitary napkins and the like.

These articles are known to typically comprise a topsheet, facing the wearer when the article is used, and a backsheet. Topsheet and backsheet are typically joined and encase the absorbent core.

The absorbent core may comprise any absorbent material that is generally compressible, conformable, non-irritating to the wearer's skin, and capable of absorbing and retaining liquids such as urine and certain other body exudates. The absorbent core may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

Preferred absorbent cores according to the present invention comprise a first material providing for a first absorbent capacity and a second absorbent material providing for a second absorbent capacity. Preferably the first material is a fibrous absorbent material and the second absorbent material is a particulate absorbent material and most preferably a superabsorbent material. Most preferably the fibrous material has a substantially uniform basis weight over the whole area of the core. If the core comprises fibrous layers which do not comprise superabsorbent material, e.g., do serve for example as acquisition or distribution layers, the basis weight of these layers does not need to be uniform, and it is preferred that only those fibrous layers which serve as containment means for superabsorbent material have uniform basis weight.

In another embodiment of the present invention the first material is not an absorbent material, i.e., its absorbent capacity is zero or essentially zero. Such a material can serve to maintain the structure and integrity of the absorbent core. For example it can be an adhesive material.

Preferably the first material is present at a low basis weight, preferably less than 130 g/m$^2$, 120 g/m$^2$, 110 g/m$^2$, 100 g/m$^2$, 90 g/m$^2$, 80 g/m$^2$, 70 g/m$^2$, 60 g/m$^2$, 50 g/m$^2$, 40 g/m$^2$ or even less than 30 g/m$^2$.

Preferred articles according to the present invention achieve a relatively narrow crotch width, which increases the wearing comfort. A preferred article according to the present invention achieves a crotch width of less than 100 mm, 90 mm, 80 mm, 70 mm, 60 mm or even less than 50 mm.

Absorbent articles are typically marketed in kits or packs comprising multiple individual absorbent articles, for example at least 10, 12, 15, 20, 25 or 30 individual absorbent articles are sold together. Consumers expect each individual absorbent article to deliver the same satisfying performance, namely in respect of absorbency. It is most critical to provide sufficient absorbency in the front half of the articles. The front half of the article is typically the area to receive discharged urine, which is then to be stored in the front half of the absorbent core.

The front half of the absorbent core should therefore comprise most of the absorbent capacity of the core. Preferably most the absorbent capacity of the core comprising a first and a second absorbent material is provided by the second absorbent material, which is preferably a particulate material and most preferably a particulate superabsorbent material. Preferably, the front half of said absorbent core comprises more than 60% of the absorbent capacity of the second absorbent material, more preferably more than 65%, 70%, 75%, 80%, 85%, 90% or 95%.

As consumers expect each individual absorbent article to deliver the same satisfying performance, but as on the other hand absorbent materials and in particular superabsorbent materials are costly, it is desirable to provide a kit or pack of individual absorbent articles wherein each individual absorbent article comprises about the same amount of absorbent materials and in particular superabsorbent materials.

An appropriate measure for the amount of absorbent material is the total weight of the absorbent material. It is desirable that the total weight of the absorbent material and namely of superabsorbent material in each individual absorbent article in a kit or pack is about the same as the average total weight of that material in the kit or pack. In other words, the standard deviation of the total weight of that material should be low. It is preferred that the standard deviation of total weight is less than 8% or less than 7%, and preferably less than 6%, and yet preferably less than 5%, and yet preferably less than 4%, and yet preferably less than 3%, and yet preferably less than 2%.

The disclosed process enables to produce kits or packs of absorbent articles with very uniform distribution of the amount of superabsorbent material.

A definition of standard deviation can be found in the book "Taschenbuch der Mathematik" by I. N. Bronstein, K. A. Semendjajew: 23. Auflage, Verlag Harri Deutsch, Thun und Frankfurt/Main (1987) ISBN 3-87144-492-8, and therein in equation (5.31) on page 666.

The present invention allows to achieve the above standard deviations where fast processes of manufacturing are employed. The above standard deviations can achieved at a production lines yielding more than 100, 200, 300, 400, 500, or even more than 600 absorbent articles per minute.

These articles are typically produced in a process of low standard deviation manufacturing for consecutive production of many absorbent articles. Not all article produced in such process may meet the desired quality standards. Some articles may be considered faulty and are therefore either manually or automatically excluded from being sold to a consumer and e.g. not packed. If, for example, eleven or twelve articles are produced and one or two articles are considered faulty, the remaining ten articles are herein considered to be consecutively produced.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of producing an absorbent article, the method comprising:
   metering particles at a predetermined flow rate to form a metered particle stream;
   carrying the metered particle stream in a carrier flow to form a carried particle stream;
   pulsing the carried particle stream through a pulsing chamber in the pulsing step at a frequency of at least 5 Hz by using a rotating separator means to form a pulsed particle stream; and
   transferring a pulse from the pulsed particle stream onto a forming surface of the absorbent article.

2. The method of claim 1, wherein the metering includes metering the particles at a predetermined constant mass flow rate to form the metered particle stream.

3. The method of claim 1, wherein the carrying includes carrying the metered particle stream in a carrier flow created by a downstream suction to form the carried particle stream.

4. The method of claim 1, wherein the pulsing includes, for each pulse:

interrupting the carried particle stream; and discontinuing the interrupting.

5. The method of claim 1, wherein the pulsing includes, or each pulse:

accumulating a portion of the carried particle stream, to form an accumulation of particles; and releasing at least a portion of the accumulation of particles, to form at least a portion of each pulse.

6. The method of claim 1, wherein the pulsing includes forming a pulsed particle stream with substantially rectangular-shaped pulses.

7. The method of claim 1, wherein the transferring includes accelerating the pulse from the pulsed particle stream in an eductor carrier flow.

8. The method of claim 1, wherein the transferring includes forming a substantially uniformly distributed pulse profile on the forming surface of the absorbent article.

* * * * *